United States Patent [19]

Bennett

[11] Patent Number: 5,269,317
[45] Date of Patent: Dec. 14, 1993

[54] INTRAVENOUS BLOOD SAMPLING APPARATUS

[75] Inventor: Elmer T. Bennett, Philadelphia, Pa.

[73] Assignee: Bennett Scientific, Inc., Philadelphia, Pa.

[21] Appl. No.: 785,905

[22] Filed: Nov. 4, 1991

Related U.S. Application Data

[63] Continuation of Ser. No. 363,248, Jun. 8, 1989, abandoned.

[51] Int. Cl.$^5$ .............................................. A61B 5/14
[52] U.S. Cl. ..................... 128/760; 128/763; 604/403
[58] Field of Search ............... 604/403, 413, 414, 415; 128/760, 761, 762, 763, 764, 765, 766

[56] References Cited

U.S. PATENT DOCUMENTS

| | | | |
|---|---|---|---|
| 3,978,846 | 9/1976 | Bailey | 128/2 F |
| 4,050,451 | 9/1977 | Columbus | 128/764 |
| 4,091,802 | 5/1978 | Columbus | 128/764 |
| 4,210,156 | 7/1980 | Bennett | 128/763 |
| 4,266,558 | 5/1981 | Akhavi | 128/766 |
| 4,266,559 | 5/1981 | Akhavi | 128/766 |
| 4,317,455 | 3/1982 | Akhavi | 128/765 |
| 4,327,745 | 5/1982 | Ford, Jr. | 128/765 |
| 4,340,067 | 7/1982 | Rattenborg | 128/763 |
| 4,367,754 | 1/1983 | Akhavi | 128/763 |
| 4,378,812 | 4/1983 | Sarstedt | 128/765 |
| 4,385,637 | 5/1983 | Akhavi | 128/763 |
| 4,393,882 | 7/1983 | White | 128/764 |
| 4,396,024 | 8/1983 | Sarstedt | 128/763 |
| 4,509,421 | 5/1986 | Ullman | 128/766 X |
| 4,589,421 | 5/1986 | Ullman | 128/763 |
| 4,660,569 | 4/1987 | Etherington | 128/765 |
| 4,703,762 | 11/1987 | Rathbone et al. | 128/763 |
| 4,731,059 | 3/1988 | Wanderer et al. | 128/765 X |
| 5,110,557 | 5/1992 | Brown et al. | 422/101 |
| 5,125,415 | 6/1992 | Bell | 128/766 |

Primary Examiner—Mickey Yu
Assistant Examiner—Sam Rimell
Attorney, Agent, or Firm—Wolf, Greenfield & Sacks

[57] ABSTRACT

An apparatus withdraws blood from a vein or artery and collects it in a collection vessel. The collection vessel includes blood inlet means and air outlet means communicating with the ambient air. The blood inlet means is adapted to accept an intravenous needle having one end ensheathed in a flexible sleeve. The blood inlet means is adapted to engage the flexible sleeve and form a seal therewith. An adaptor holds the intravenous device and collection vessel together.

6 Claims, 3 Drawing Sheets

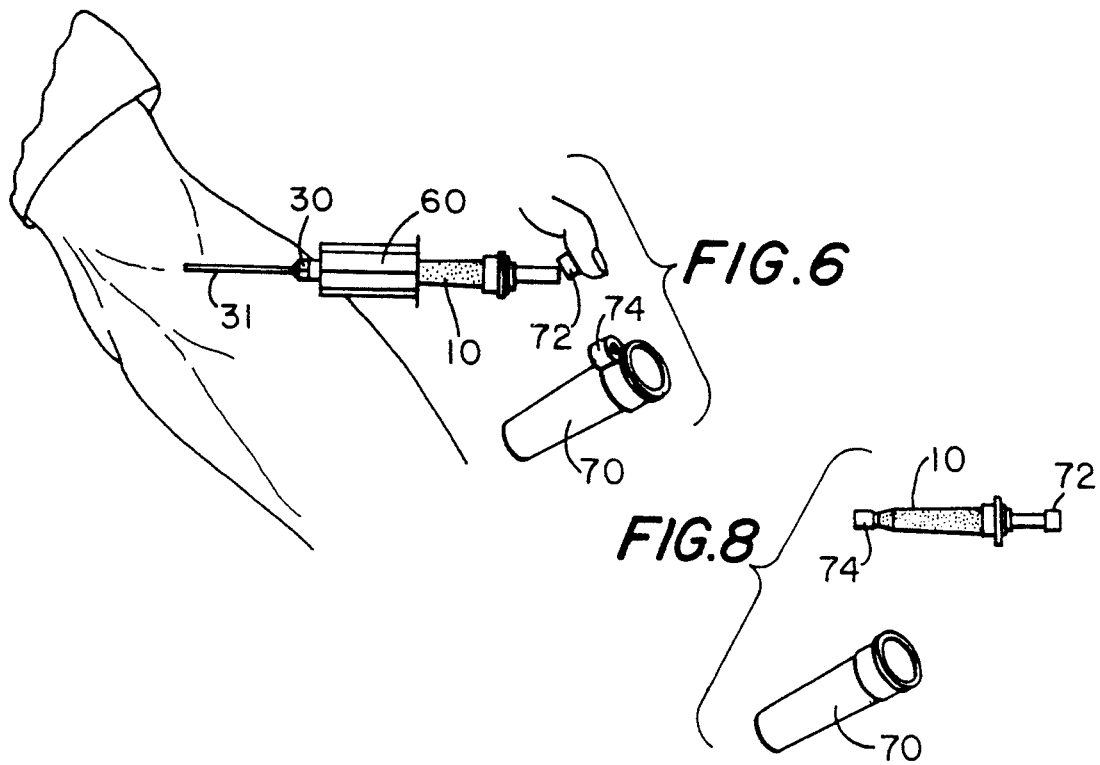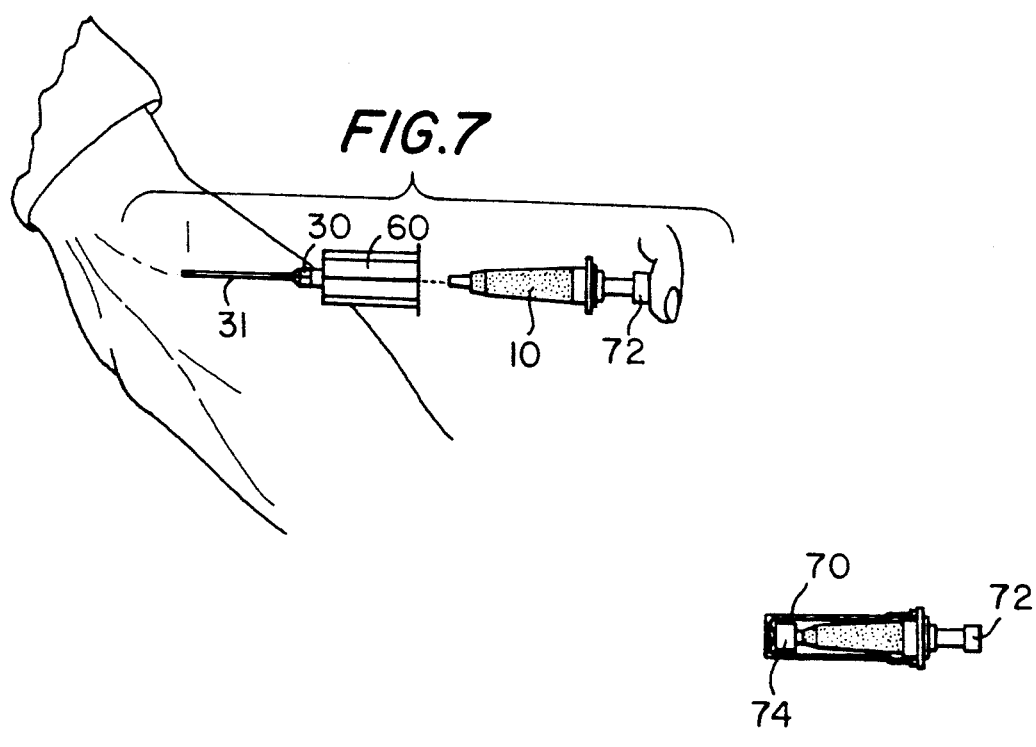

INTRAVENOUS BLOOD SAMPLING APPARATUS

This is a continuation of co-pending application Ser. No. 07/363,248 filed on Jun. 8, 1989, now abandoned.

FIELD OF THE INVENTION

This invention relates to a blood collection vessel adapted to accept an intravenous needle to allow collection of blood by the venous pressure of the circulatory system.

BACKGROUND OF THE INVENTION

U.S. Pat. No. 4,210,156 to Elmer T. Bennett shows a blood sampler for collecting up to two milliliters of blood. This sampler functions by piercing the skin superficially and using a vacuum effect to collect the resulting small pool of blood formed on the skin surface. The vacuum for this sampler is created by the operator sucking on a mouthpiece. The sampler includes a collection vessel for containing the blood sample. The vessel includes a substantially transparent tapered end portion and a top portion. The two portions are assembled to form a single cavity. The tapered end portion has an opening through which blood enters from the skin surface. The top portion has a channel which communicates with the suction tube.

A variation on the Bennett '156 sampler is shown in FIG. 1 herein. This sampler is includes a small projection 11 that extends outward from the rim of the inlet tip of the tapered portion of the collection vessel. This outward projection is effective for collecting the small pool of blood from the skin surface.

Becton, Dickinson & Co. of Shipshewana, Ind., markets a device under the trademark "Vacutainer". This device generally comprises three parts: an intravenous needle portion, a vacuum tube, and a holder. The intravenous needle portion includes a length of hollow metal tubing, one end of which forms a skin-piercing intravenous needle and the other end of which is ensheathed in a flexible sleeve. This ensheathed end is designed to pierce a rubber stopper in the vacuum tube which forms a collection vessel. The vacuum tube is an evacuated glass testtube. The holder holds the vacuum tube in place relative to the intravenous needle so that the vacuum tube may be pressed down on the ensheathed end thereof. In operation, the skin piercing end of the intravenous portion is inserted into a vein. Once the tip of the intravenous needle has pierced the vein, the vacuum tube is firmly pushed forward in the holder so that the ensheathed end of the needle is forced through the rubber top of the vacuum tube as the sleeve surrounding the needle is compressed. The vacuum tube must be pushed down firmly in order to pierce the rubber top. This operation requires a substantial degree of manual dexterity on the part of the phlebotomist. Blood is drawn through the needle and into the vacuum tube by a suction force created by the vacuum inside the tube.

The "Vacutainer" device is designed to sample relatively large quantities of blood, compared to the '156 sampler. Like the '156 sampler, the "Vacutainer" device uses a vacuum principle to extract blood, but because it extracts blood by artificial suction through the needle, it has numerous disadvantages.

It is known that blood cells may be damaged in the course of vacuum-drawing, thus affecting the integrity of later analysis. For example, hemolysis of red blood cells may occur as the cells are forced under pressure through the narrow orifice of the drawing needle. Thus, vacuum blood-drawing is generally conducted through larger gauge needles, in order to minimize hemolysis. Larger gauge needles are relatively more uncomfortable to the patient.

In addition to hemolysis of red blood cells, vacuum drawing may result in other abnormalities which tend to confound interpretation of data relying on visual examination of cells, e.g. as in the differential leukocyte count. The appearance of cell abnormalities or cell fragments, which may be regarded as an indication of illness, may actually comprise artifact caused in the vacuum drawing process. For instance, red blood cell abnormalities such as clumping or stacking, which may otherwise be indicative of disease, may in actuality be caused by the drawing process, and not any disease.

Another disadvantage of vacuum tube samples may occur when the vacuum is lost for any reason during the blood-drawing process. If this occurs, the needle must be withdrawn from the patient, and the procedure must be repeated.

The use of vacuum tubes may also increase health hazards to both laboratory technicians and the general public. For example, small amounts of blood emit from the needle hole in the vacuum tube's rubber top as the collection tube is withdrawn from operative engagement with the sheathed needle. Contact with even these minute amounts of blood may be hazardous to health care personnel. Particularly, contact may be incurred with highly infectious specimens, such as specimens withdrawn from hepatitis patients, AIDS patients and the like. Moreover, it has been observed that when the rubber top of a vacuum tube is removed in the laboratory for sampling, the rapid equalization of pressure between the still partially evacuated tube and the atmosphere may cause blood aerosols to be emitted. Contact by laboratory personnel with these vapors may be hazardous.

Vacuum blood-drawing may also result in a distorted analysis of blood components. Samples drawn under vacuum may indicate a disproportionately high level of the lighter blood components such as platelets, immature cells and blood gases. These lighter blood components, particularly blood gases, are withdrawn at a higher rate than the heavier components. The levels of the lighter blood components may thus be artificially enriched in the sample. As a result, blood samples for gas analysis are typically drawn in specialized syringes, and only from arterial blood sources.

Additionally, since blood rushes into evacuated tubes at a relatively rapid rate, the amount of blood drawn by means of vacuum tubes may not be controlled with precision.

The preferential enrichment of lighter blood components in vacuum tube samples is particularly troublesome when like volume samples must be drawn from the same patient at various time intervals. The inability to accurately draw precisely the same volume of blood each time using vacuum tubes, coupled with the selective enrichment of the lighter blood components inherent in vacuum-drawing, may confound interpretation of such serially-drawn samples.

Vacuum tubes are typically fabricated from glass, and are generally sized for drawing 5, 10 and 15 ml specimens. The use of glass containers for blood-sampling has several disadvantages. First, they must be centrifuged only at relatively slow speeds, about 3,500 r.p.m. Second, vacuum tubes are not easily marked for identification purposes. This make illegally disposed medical waste contained in vacuum tubes difficult to trace. Third, vacuum tubes have limited shelf life, since the vacuum is inevitably lost through prolonged storage. Fourth, for analyses requiring uncoagulated blood, vacuum, tubes contain anticoagulant which is deposited in the tube bottom as a liquid, solid or powder. Because of the manner in which vacuum tubes are filled, the anticoagulant may not mix evenly with the blood, resulting in coagulation of some portions of the sample.

Newer blood analysis equipment requires smaller specimens (generally 5 to 20 microliters) than the relatively large blood volumes typically drawn with vacuum tubes. This excess blood, which is not used, increases the cost of medical waste processing. Typically, blood collected in vacuum tubes must be thereafter transferred to smaller containers designed for use in the various laboratory analyzers. Such additional manipulative steps and handling of blood samples is undesirable from the standpoints of laboratory efficiency and safety.

Finally, in elderly persons and neonates, it may be impossible to utilize vacuum tube type collection. The relatively strong vacuum may lead to collapse of the vein being sampled. Moreover, it is known that the sudden surge of blood flow into evacuated collection tubes is stressful to the cardiac system of neonates and infants, and may result in cardiac arrest.

SUMMARY OF THE INVENTION

An apparatus for withdrawing and collecting blood from a vein or artery is provided. A collection vessel having blood inlet means and air outlet means communicating with the ambient air forms a blood collection chamber between the inlet and outlet means. An intravenous needle assembly comprising an intravenous needle is removably connected to the collection vessel through the blood inlet means.

The collection vessel of the present invention is designed to be used in conjunction with an intravenous needle having a skin-piercing end and an ensheathed end. At approximately the mid-point of the needle is a collar having screw threads. The ensheathed end is ensheathed in an axially-deformable sleeve which covers substantially the entire portion of the needle between the collar and the end point. The skin-piercing end of the needle is inserted in a blood vessel such as a vein or artery. The ensheathed end is inserted into the blood inlet means and into the blood collection chamber of the collection vessel. The inlet means of the collection vessel includes means for axially compressing the deformable sleeve so that the tip of the intravenous needle will be exposed within the cavity of the collection vessel when the ensheathed end is inserted into the inlet means. The engagement of the compressed sleeve with the inlet opening causes a substantially leak-proof seal to be formed between the intravenous needle and the perimeter of the inlet opening of the collection vessel. Thus, blood will flow directly from a blood vessel, through the intravenous needle, and into the collection vessel with minimal risk of leakage.

In this invention, when blood is being extracted from a blood vessel, the ventilation opening of the collection vessel is left open to the atmosphere. Instead of drawing blood out of the vein by a vacuum, the apparatus allows the blood to travel into the collection vessel solely by the veinous pressure of the circulatory system. When the ventilation opening is closed by a user, displacement of air from within the cavity is prevented, and thus the flow of blood into the collection vessel will stop. The present invention, therefore, allows for a relatively accurate control of blood flow from a blood vessel into the collection device.

An advantage of the present invention is that it provides an intravenous blood sampling apparatus which minimizes the risks associated with use of vacuum tubes. The present invention, because it does not require vacuum-forcing of blood through a needle, prevents cell distortion, particularly red blood cell stacking, clumping and hemolysis. The device may be utilized for drawing and accurately determining the level of all blood components, including blood gases. Further, the present invention allows the use of smaller-gauge, less uncomfortable needles. The invention also eliminates many, if not all, of the other disadvantages of vacuum tube blood-sampling and known intravenous sampling devices, such as the aerosol emission of blood upon opening of the vacuum tube.

DESCRIPTION OF THE DRAWINGS

For the purpose of illustrating the invention, there is shown in the drawings a form which is presently preferred; it being understood, however, that the invention is not limited to the precise arrangements and instrumentalities shown.

FIGS. 6-9 show a sequential method of use and assembly of the apparatus of the present invention.

DETAILED DESCRIPTION OF THE INVENTION

Figures 1, 2, 10:
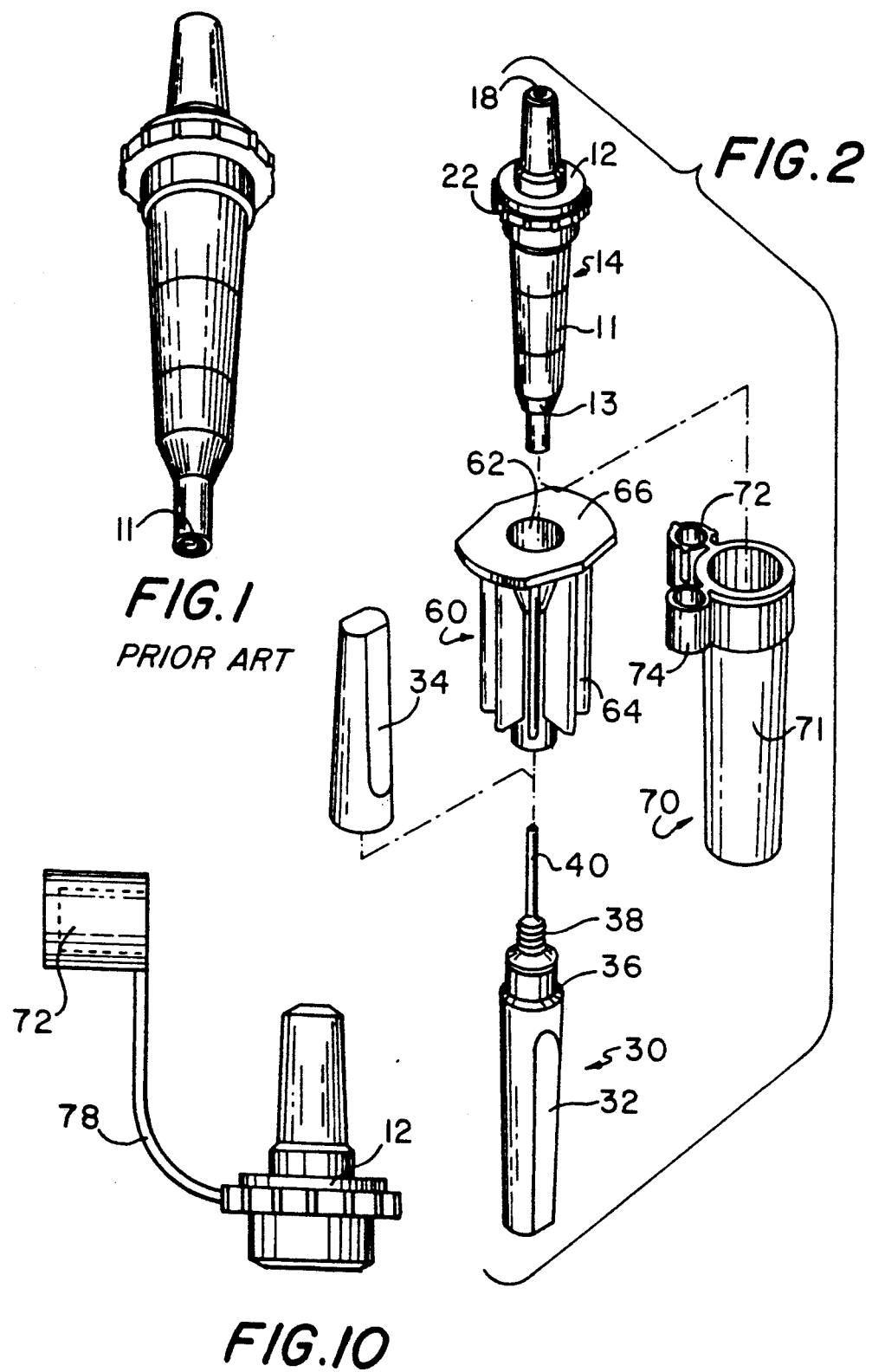
FIG. 1 is an isometric view of a prior art collection vessel.
FIG. 2 is an exploded view of an apparatus in accordance with the present invention.
FIG. 10 shows an alternate embodiment of the present invention.

Referring to the drawings in detail, wherein like numerals indicate like elements, there is shown in FIGS. 2-5 the apparatus of the present invention. The invention comprises a collection vessel generally designated as 10, along with an intravenous needle assembly 30, a holder 60, and a transport container 70.

The collection vessel 10 comprises a removable top 12 which snaps onto a tapered tube 14. Top 12 has an opening 21 which communicates with the cavity 20 of tube 14 through passageway 18. Opening 21 serves as a ventilation opening for cavity 20. Top 12 is preferably formed by an injection-molding process from a polymeric plastic which may be color-coded to suit clinical laboratory color-coding standards. Top 12 includes an outer rim 22 of a relatively wide diameter as compared to tube 14 or passageway 18. Top 12 is generally shaped to allow the collection vessel 10 to be handled by top 12.

According to one embodiment, tapered tube 14 comprises a multi-tapered tube having a first tapered diameter portion 11, which comprises the main body portion of the tube. Tapered diameter portion 11 terminates in a second, more tapered diameter portion 13 which forms a frusto-conical body portion. Frusto-conical portion 13 may serve to secure the collection vessel 10 in the inner cavity 62 of holder 60, which will be discussed below. Frusto-conical portion 13 terminates in a third, fixed diameter body portion, which forms tip 16. Tip 16 contains a channel 19 adapted for receiving an intravenous needle for the passage of blood into cavity 20. Tapered tube 14 preferably is made of a substantially translucent polymeric plastic, so that blood may be observed entering cavity 20. Tapered tube 14 may be secured to top 12 by any of several known means to effect a seal, such as lip 15 in the top of tapered tube 14, which contacts the interior of a rim 15a in cap 12. A stop means or screw means (not shown) may also be used as desired.

The two-piece construction of collection vessel 10 allows for advantages in blood analysis. A probe may be inserted into tapered tube 14 to remove a portion of the sample. To improve the functioning of the apparatus, the interior surface of collection vessel 10 may be coated with a known anticoagulant, such as EDTA, sodium or potassium oxalate, or sodium or potassium citrate.

Intravenous needle assembly 30 comprises an intravenous needle 35, which has a skin-piercing end 31, and an ensheathed end 41. A collar 36 encircles the shaft of the intravenous needle 35, dividing the intravenous needle 35 into the two ends. Collar 36 has a threaded portion 38 on the side adjacent the ensheathed end of the intravenous needle 35. Intravenous needle 35 is preferably formed from a single piece of narrow tubing, but conceivably, the skin-piercing end and the ensheathed end may be formed by two separate pieces of tubing of different gauges joined at collar 36, depending on specific needs. In FIG. 2, the intravenous needle assembly 30 is shown in conjunction with protective covers 32 and 34, which fit over the skin-piercing and ensheathed ends respectively, for easy handling and for maintaining sterilization.

The axially-deformable sleeve 40 around the ensheathed end 41 of the intravenous needle 35 substantially completely envelops the ensheathed end 41. When the ensheathed end 41 is inserted into the opening at the end of tip 16 of collection vessel 10, which opening forms a blood inlet means, the deformable sleeve 40 will be engaged by the perimeter of the opening, axially compressing the sleeve down needle 35 and away from the needle point of ensheathed end 41. The point will pierce the end of sleeve 40 as the previously ensheathed end of the needle passes through the inlet means 16 and into the cavity 20 of collection vessel 10.

Sleeve 40 is preferably made of a resilient material, such as latex, which will re-form a substantial seal at the tip of sleeve 40 when the ensheathed end 41 is withdrawn from inlet means 16 of collection vessel 10. Upon withdrawal, sleeve 40 will return to its original shape and there will not be a significant leakage of blood from the ensheathed end 41 even after the tip of sleeve 40 is pierced.

Figure 3:
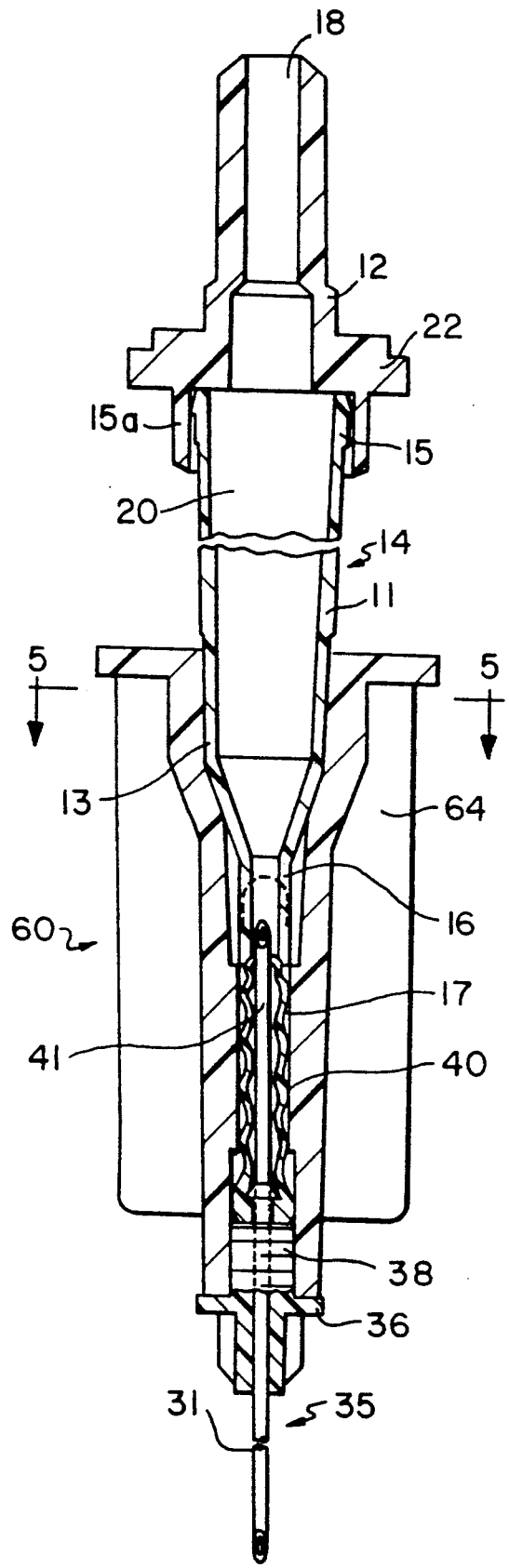
FIG. 3 is a cross-sectional view of the apparatus shown in FIG. 2.
Figure 5:
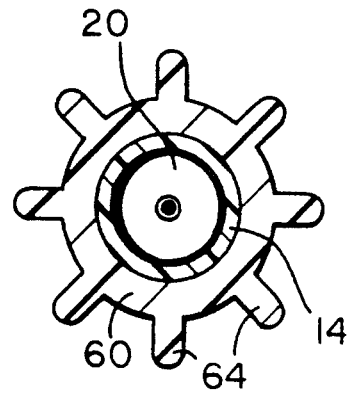
FIG. 5 is a cross-sectional view through line 5—5 of FIG. 3.
Figure 4:
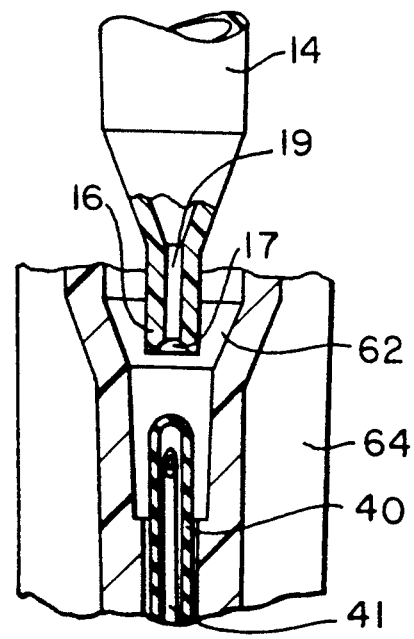
FIG. 4 is an enlarged cross-sectional view of a portion of the present invention.

Intravenous needle assembly 30 screws onto one end of holder 60 by means of engagement of the threaded portion 38 of collar 36 with matching threads (not shown) on holder 60. The collection vessel is then inserted through the other end of holder 60 and pushed forward into operative engagement with the ensheathed end 41 of intravenous needle 35. The completed assembly is shown in FIG. 3. Thus, the bore of holder 60 forms a channel 62 wherein collection vessel 10 and intravenous device 30 are operatively held together. Holder 60 further comprises a flange 66 and a plurality of radially extending fins 64 which allow the whole assembly (collection vessel 10, intravenous needle assembly 30, and holder 60) to be held easily in the fingers.

A portion of channel 62 in holder 60 preferably conforms to the shape of the frusto-conical portion 13 of tapered tube 14, so that tapered tube 14 will fit securely in channel 62. With this arrangement, channel 62 will form a stop means with frusto-conical portion 13, so that when collection vessel 10 is inserted into holder 60 and into engagement with the ensheathed portion of needle 35, the collection vessel 10 is inserted just far enough to compress the sheath to uncover the opening in the ensheathed end of needle 35. By limiting the insertion of the needle to the minimum necessary amount, sleeve 40 will be deformed minimally so that it will easily resume its original shape when the collection vessel is removed. The axially compressed sleeve also functions to provide a seal between needle 35 and the bore of the holder.

In the preferred embodiment, the inlet means 16 of collection vessel 10 comprises a channel 19 which terminates in a counterbore 17 at its outer end. Counterbore 17 is a hemispherical cavity designed to engage and axially compress the flexible sleeve 40 when the ensheathed end 41 of needle 35 is inserted into channel 19. Counterbore 17 and channel 19 are of such dimensions that, when the ensheathed end 41 of needle 35 is inserted, the needle itself will fit through the channel 19 while the sleeve 40 will be engaged by the counterbore 17, as can be seen in FIG. 3. The compressed flexible sleeve 40 will, by natural resilience, urge into the counterbore 17 and thus serve as a gasket around needle 35. The seal formed by this gasket is leak-proof in regards to both blood and air. Thus, blood entering cavity 20 through needle 35 will not seep through the space between channel 19 and the outer surface of the needle. Also, because the seal is leakproof in regards to air, no air exchange can take place through the inlet means 16 of collection vessel 10. Any air displacement caused by the entry of blood through needle 35 must be through passageway 18.

Collection vessel 10 is adapted to fit in transport container 71, which is part of receptacle means 70. Receptacle means 70 comprises transport container 71, and caps 72 and 74, which are attached to the rim of transport container 71, as shown in FIG. 2. The rim of transport container 71 is adapted to engage the diameter of top 12. Vessel 10 is inserted into transport container 71 in which a filled collection vessel may be transported safely to a laboratory. When the collection vessel is full, plug 74 is broken off transport container 71 and placed over the tip of vessel 10. Cap 72 is likewise broken off from transport container 71 and placed over top 12, sealing the passageway 18 therein. The vessel is then inserted into the transport container 71 and secured therein.

The advantage of the present invention is that blood can be withdrawn from a vein or artery without the disadvantages of artificial suction, as from a vacuum device. Blood enters collection vessel 10 through the venous pressure of the circulatory system, displacing the air under ambient pressure within the collection vessel 10. The flow of blood into collection vessel 10 can be accurately controlled by means of stopping or starting the air displacement within the collection vessel 10. In order for this type of control to work properly, it is important that the inlet means 16 of the collection vessel 10 form a tight seal around the intravenous needle 35. Flexible sleeve 40, when it is compressed down along the shaft of the needle, deforms and fills recess 17 to form a leak proof seal both to blood and to air. Manifestly, blood can enter the cavity 20 through needle 35 only; air in collection vessel 10 can be displaced only through passageway 18.

When extracting blood from a vein or artery the flow of blood into collection vessel 10 is controlled by allowing or preventing air displacement from collection vessel 10 through ventilation passageway 18. Blood will flow into the collection vessel 10 by the force of the venous pressure of the circulatory system, as long as air displacement is allowed. Thus, when passageway 18 is opened to the atmosphere, blood entering collection vessel 10 will push the air normally in collection vessel 10 out through passageway 18 as it fills collection vessel 10. However, if the air normally in collection vessel 10 has no means of escaping, blood will not be able to fill the collection vessel 10.

FIGS. 6 through 9 show a sequence of steps by which the apparatus is assembled and used, in this case in extracting blood from a vein in the arm. FIG. 6 shows the assembly of intravenous needle assembly 30, holder 60, and collection vessel 10, put together to form a collection device which is inserted in a vein.

In practice, it has been found that the most convenient way of regulating the blood flow is to place cap 72 loosely over the opening 21 in collection vessel top 12, then pushing it down firmly to seal the opening when one wishes the blood flow to stop. In FIG. 6 cap 72 is shown loosely placed on the top of top 12.

When collection vessel 10 is full, the user presses cap 72 firmly down over collection vessel top 12, stopping air exchange and preventing the further flow of blood into the collection vessel 10. If it is desired to fill multiple collection vessels with the subject's blood, collection vessel 10 may be removed from holder 60 and thus disconnected from intravenous needle 35, while leaving the intravenous needle 31 in the patient's arm, as shown in FIG. 7. The flexible sleeve 40 around the intravenous needle will, when the collection vessel 10 is removed, return to its original position around the rearward tip of the needle, and prevent leakage of blood when the collection vessel is removed. While skin-piercing end 31 of intravenous needle 35 is still in the patient's arm, another collection vessel 10 may be forced down over the needle, to be filled in a similar fashion.

When the collection vessel 10 is removed, cap 74 is advantageously detached from its frangible connection with transport container 71, and placed over tip 16 of collection vessel 10, thus insuring that the blood will not be spilled. The entire collection vessel 10, with cap 72 and cap 74, is then placed in a transport container 71, as shown in FIG. 9. The collection vessel 10 is then taken to a lab, where the exposed cap 12 may be viewed by lab personnel and sorted by a color code.

FIG. 10 shows an alternate embodiment of collection vessel top 12, designated 12', wherein the cap 72' is connected to top 12' by means of a thin plastic strip 78. This arrangement facilitates an easier securing of cap 72' onto top 12', and insures that loose caps will not litter the laboratory.

The blood in the vein enters collection vessel 10 of the present invention solely by the force of the venous pressure of the circulatory system. Unlike most previous intravenous devices, there is no artificial vacuum created by the present invention. One advantage of the invention is that accurate measurement of all blood components, including lighter components such as bloods gases, may be accomplished. When a fresh blood sample is exposed to an artificial vacuum, the change in pressure against the surface of the blood may liberate a portion of the dissolved gases from the blood. Because the collection vessel of the present invention is filled only by the passive displacement of air, and not by means of vacuum, gases will tend to remain dissolved in the sample during the drawing procedure. Consequently a measurement of those gases will be more accurate.

Moreover, the gentle drawing of blood samples with the device of the invention ensures that the various cell types found in blood remain intact, without the clumping, stacking, fragmentation which may be caused by conventional vacuum drawing produces.

The passive displacement of air within the collection vessel in the present invention eliminates many of the disadvantages associated with vacuum tube blood-drawing. Whereas vacuum tubes depend on the suction in an evacuated tube to remove the blood from a blood vessel, a user of the present invention would not have to worry about a loss of suction disrupting the flow of blood. The health hazards to laboratory workers as a result of airborne blood carrying infectious diseases are minimized with the present invention, because the lack of a vacuum inside the tube avoids release of blood aerosols from the sample when the container is open to the atmosphere.

Because it is contemplated that the container is constructed of plastic, it may be centrifuged at higher speeds than a glass container without danger of breaking, and therefore centrifugation times are much shorter for the containers of the present invention than for the glass tubes of the prior art. Also, the plastic containers of the present invention may be easily marked for identification purposes, which will facilitate tracing of illegally disposed medical waste.

Since the container fills more slowly than vacuum tubes, and since the plastic construction allows anticoagulant to be coated onto the container walls, a more even mixing of blood and anticoagulant is achieved, than in vacuum tubes wherein free flowing anticoagulant tends to localize in one area of the tube during the drawing process.

The present invention may be embodied in other specific forms without departing from the spirit or essential attributes thereof and, accordingly, reference should be made to the appended claims, rather than to the foregoing specifications, as indicating the scope of the invention.

I claim:

1. An apparatus for withdrawing and collecting blood from a vein or artery comprising:
   (a) an intravenous needle assembly comprising an intravenous needle having a skin-piercing end and a second end, the intravenous needle forming a conduit therewith for the passage of blood, wherein the second end of the intravenous needle is ensheathed in an axially deformable sleeve;
   (b) a collection vessel comprising a collection tube having a detachable top, the collecting tube and attachable top defining a blood-collecting chamber, the collecting tube having an inlet opening adapted to receive the second end of the intravenous needle, the detachable top having a ventilation opening therein; and (c) an adapter for holding the intravenous needle in the inlet opening;

(d) whereby blood is drawn from the vein or artery through the intravenous needle assembly into the collection vessel solely by the pressure of the circulatory system.

2. An apparatus according to claim 1 further comprising means for axially compressing the deformable sleeve.

3. An apparatus according to claim 2 wherein the means for axially compressing the deformable sleeve comprises a bore in the inlet opening of the collection tube to permit the second end of the intravenous needle to pass therethrough, and a counterbore in said inlet opening for engaging the deformable sleeve.

4. An apparatus for the intravenous collection of blood comprising:
(a) an intravenous needle assembly comprising an intravenous needle held by a collar having thread means thereon, said collar located at a distance from one end of said needle, the portion of the needle on one side of the collar being adapted for piercing the skin, the portion of the needle on the opposite side of the collar being ensheathed in a flexible sleeve;
(b) a collection vessel comprising a multi-tapered collection tube and a detachable top forming a blood-collection cavity, said tube having a first tapered diameter portion, a second tapered diameter portion and a third reduced diameter portion which terminates in a blood inlet means, said detachable top having a ventilation opening therein, said blood inlet means of the tube having a bore adapted to permit the ensheathed portion of the needle to pass therethrough, and a counterbore having a substantially hemispherical cavity for engaging and axially compressing the flexible sleeve to expose the bore of the intravenous needle so blood may flow through the intravenous needle into the collection vessel;
(c) an adaptor for holding the intravenous assembly and collection vessel together, said adaptor having a bore which has a first diameter portion, a tapered second diameter portion, and a third portion of reduced diameter terminating in a threaded portion for threaded engagement with the collar of the intravenous needle assembly to secure said assembly to the adaptor, said tapered second diameter portion of the adaptor bore having substantially the same taper as the tapered second diameter portion of the collection tube;
(d) a transport container for containing the collection vessel when the collection vessel is removed from the adaptor and intravenous needle assembly; and
(e) first and second cap means adapted for closing the blood inlet opening of the collection tube and the ventilation opening of the collection tube cap.

5. An apparatus according to claim 4 wherein the first and second cap means are connected to the exterior of the transport container by means of frangible tabs.

6. An apparatus according to claim 4 wherein the cap means for closing the ventilation inlet opening is connected to the collection tube top by a flexible strap.

* * * * *